(12) United States Patent
Yamamoto et al.

(10) Patent No.: US 11,944,525 B2
(45) Date of Patent: Apr. 2, 2024

(54) ABSORBENT ARTICLE

(71) Applicant: KAO CORPORATION, Tokyo (JP)

(72) Inventors: Ryoichi Yamamoto, Utsunomiya (JP);
Mina Tomita, Utsunomiya (JP);
Takuya Kouta, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 638 days.

(21) Appl. No.: 17/277,545

(22) PCT Filed: Sep. 5, 2019

(86) PCT No.: PCT/JP2019/034891
§ 371 (c)(1),
(2) Date: Mar. 18, 2021

(87) PCT Pub. No.: WO2020/059507
PCT Pub. Date: Mar. 26, 2020

(65) Prior Publication Data
US 2021/0346214 A1    Nov. 11, 2021

(30) Foreign Application Priority Data

Sep. 19, 2018  (JP) .................................. 2018-175051
May 31, 2019   (JP) .................................. 2019-102728

(51) Int. Cl.
*A61F 13/511*       (2006.01)

(52) U.S. Cl.
CPC .... *A61F 13/51104* (2013.01); *A61F 13/5116* (2013.01); *A61F 2013/51178* (2013.01)

(58) Field of Classification Search
CPC ............. A61F 13/1104; A61F 13/5116; A61F 13/511; A61F 13/514; A61F 13/515; A61F 2013/51178
See application file for complete search history.

(56) References Cited

U.S. PATENT DOCUMENTS

| 6,454,747 B1 | 9/2002 | Shimada et al. |
| 2008/0137977 A1 | 6/2008 | Bertens et al. |
| 2008/0294135 A1 | 11/2008 | Hara et al. |
| 2016/0074259 A1 | 3/2016 | Rosati et al. |

(Continued)

FOREIGN PATENT DOCUMENTS

| CN | 102395344 A | 3/2012 |
| CN | 206508131 U | 9/2017 |
| CN | 197813925 A | 1/2018 |

(Continued)

OTHER PUBLICATIONS

International Search Report for PCT/JP2019/034891 dated Oct. 8, 2019.

*Primary Examiner* — Benjamin J Klein
*Assistant Examiner* — Hans Kaliher
(74) *Attorney, Agent, or Firm* — Birch, Stewart, Kolasch & Birch, LLP

(57) ABSTRACT

An absorbent article 1 includes a three-dimensionally shaped topsheet 2 having projections 24 and recesses and a backsheet 3. Opposed end flaps 1E in longitudinal end portions are formed of at least the topsheet 2 and the backsheet 3. In at least one of the longitudinal end portions, a plurality of the projections 24 of the topsheet 2 protrude outward in the longitudinal direction X beyond the end edge e1 of the backsheet.

9 Claims, 4 Drawing Sheets

(56) References Cited

U.S. PATENT DOCUMENTS

| | | | |
|---|---|---|---|
| 2017/0216111 A1* | 8/2017 | Kleuskens | ............. A61F 13/49 |
| 2018/0133072 A1 | 5/2018 | Uda et al. | |

FOREIGN PATENT DOCUMENTS

| | | | | |
|---|---|---|---|---|
| EP | 3 437 607 A1 | 2/2019 | | |
| GB | 2559705 A | 8/2018 | | |
| JP | 11-299829 A | 11/1999 | | |
| JP | 2000-189454 A | 7/2000 | | |
| JP | 2009-100878 A | 5/2009 | | |
| JP | 2009-136349 A | 6/2009 | | |
| JP | 2013-154016 A | 8/2013 | | |
| JP | 2018-7954 A | 1/2018 | | |
| JP | 6275364 B1 * | 2/2018 | ............. | A61F 13/47 |
| RU | 144 245 U1 | 8/2014 | | |
| WO | WO-0147460 A1 * | 7/2001 | ......... | A61F 13/4752 |
| WO | WO 2005/120411 A1 | 12/2005 | | |
| WO | WO 2017/086076 A1 | 5/2017 | | |
| WO | WO-2017086327 A1 * | 5/2017 | ............ | A61F 13/511 |
| WO | WO 2018/003126 A1 | 1/2018 | | |
| WO | WO 2018/051518 A1 | 3/2018 | | |

* cited by examiner

ABSORBENT ARTICLE

TECHNICAL FIELD

The present invention relates to an absorbent article.

BACKGROUND ART

Known techniques for improving wearer comfort of an absorbent article include treating longitudinal end edges of the absorbent article. For instance, patent literature 1 listed below, which is assigned to the same assignee of this patent application, discloses an absorbent article having a topsheet extending longitudinally outward from the ends of each of an absorbent member and a backsheet. The absorbent article offers the advantage that a discomfort feeling caused by the longitudinal ends of an absorbent article contacting the wearer's skin is reduced.

Patent literature 2 discloses an absorbent article having a liquid-permeable topsheet and a backsheet both extending outward from the longitudinal ends of an absorbent member, the topsheet further extending outward from each longitudinal end of the backsheet to form an end extension. The absorbent article is described as having the ends of the backsheet out of direct contact with the skin and thereby reducing wearer discomfort.

CITATION LIST

Patent Literature

Patent literature 1: JP 2009-100878A
Patent Literature 2: JP 2013-154016A

SUMMARY OF INVENTION

The present invention relates to an absorbent article including a three-dimensionally shaped topsheet having projections and recesses and a backsheet and having a longitudinal direction corresponding to the front-to-back direction of a wearer and a lateral direction perpendicular to the longitudinal direction. The opposed longitudinal end portions of the absorbent article are each composed of at least the topsheet and the backsheet. A plurality of the projections of the topsheet protrude or extend longitudinally outward beyond the end edge of the backsheet in at least one of the longitudinal end portions.

DESCRIPTION OF EMBODIMENTS

In order to furnish absorbent articles having further improved wearer comfort, it has been demanded to further reduce a strange feeling or discomfort that may be caused by the contact of the end edges of the article with the wearer's skin.

The present invention relates to an absorbent article that is less likely to cause wearer discomfort when an end edge of the article comes in contact with the wearer's skin.

Figure 1:
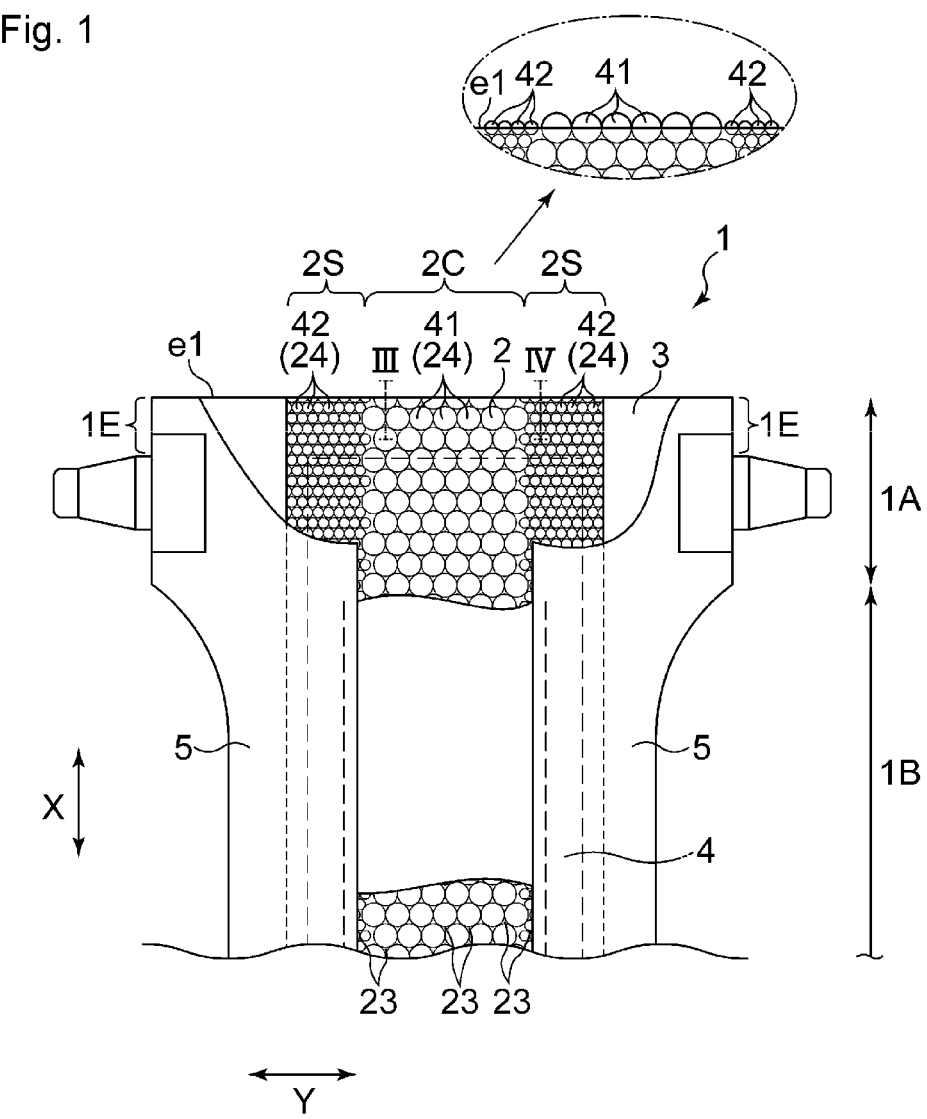
FIG. 1 is a schematic plan of an open-style disposable diaper as an embodiment of the absorbent article of the present invention, with part cut away.

The present invention will be described on the basis of its preferred embodiments with reference to the accompanying drawings. FIG. 1 schematically illustrates the structure of an open-type disposable diaper, which is one embodiment of the absorbent article according to the present invention. The diaper 1 shown in FIG. 1 has an oblong shape having a longitudinal direction X corresponding to the direction extending from the front to the back via the crotch of a wearer and a lateral direction Y perpendicular to the longitudinal direction X. The diaper 1 has a rear region 1A adapted to be worn about the back of a wearer, an unshown front region adapted to be worn about the front of a wearer, and a crotch region 1B located between the rear and front region and adapted to be worn about the crotch of a wearer. The crotch region 1B has a target zone where the bodily discharges will be located.

As illustrated, the diaper 1 has both the lateral side edges of the rear region 1A and the unshown front region located laterally outward of the lateral side edges of the crotch region 1B. Each lateral side edge of the crotch region 1B is inwardly concave in an arc. In other words, the diaper 1 generally has an hourglass shape, with the longitudinal middle portion narrowed.

As illustrated, the diaper 1 includes a liquid retentive absorbent member 4 that is oblong in the longitudinal direction X, a topsheet 2 on the skin facing side of the absorbent member 4, and a backsheet 3 on the non-skin facing side of the absorbent member 4. The topsheet 2 and the backsheet 3 both extend outward from each lateral side edge and each longitudinal end of the absorbent member 4 and are bonded to each other in the extended region outside the perimeter of the absorbent member 4 thereby to fixedly hold the absorbent member 4 between them. A pair of side sheets 5 that form a pair of cuffs on the skin facing side of the topsheet 2 are fixedly overlaid on either lateral side of the topsheet 2 along the longitudinal direction X.

As used herein, the term "skin facing side" refers to the side facing the wearer's skin while worn, i.e., the side relatively closer to the wearer's skin, and the term "non-skin facing side" refers to the side facing away from the wearer's skin while worn, i.e., the side relatively farther from the wearer's skin.

As illustrated, the diaper 1 has an end flap 1E outward of the longitudinal end of the absorbent member 4 in a longitudinal end portion located in each of the rear region 1A and the unshown front region. The end flap 1E is a laterally oblong region that extends in the lateral direction Y. The end flap 1E is composed of a plurality of sheet materials including the topsheet 2 and the backsheet 3. For instance, the end flap 1E of the embodiment is composed of the topsheet 2, the backsheet 3, and the pair of side sheets 5.

FIGS. 1 through 4 show an example of the topsheet 2 used in the embodiment. The illustrated topsheet 2 has a three-dimensional structure having a plurality of projections projecting toward the skin of a wearer while worn and a plurality of recesses each defined between adjacent projections. The topsheet 2 has a laminate structure composed of an upper nonwoven fabric sheet 21 on the skin facing side and a lower nonwoven fabric sheet 22 on the non-skin facing side, the upper and the lower nonwoven fabric sheets 21 and 22 are united together at a plurality of bonds 23. The upper nonwoven fabric sheet 21 bulges away from the lower nonwoven fabric sheet 22 to form a large number of projections 24 at the sites other than the bonds 23. Each bond 23 located between adjacent projections 24 defines the bottom of each recess of the three-dimensional structure of the topsheet 2. The upper nonwoven fabric sheet 21 that defines the skin facing side of the topsheet 2 thus forms the three-dimensional structure.

Figure 2:
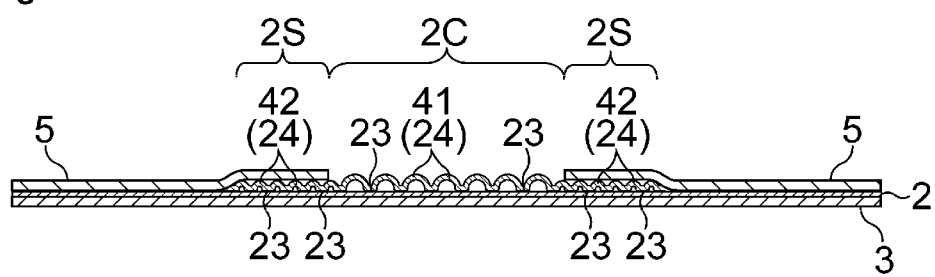
FIG. 2 is an end view of the end flap shown in FIG. 1.
Figure 3:
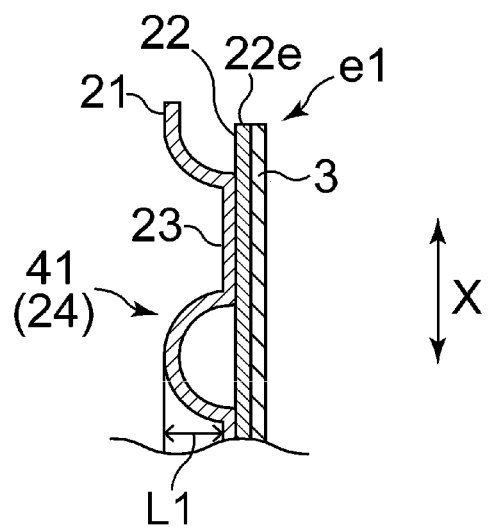
FIG. 3 is a cross-section taken along line in FIG. 1.
Figure 4:
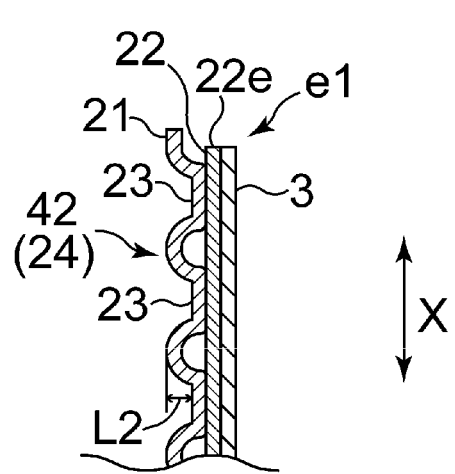
FIG. 4 is a cross-section taken along line IV-IV in FIG. 1.

On the other hand, the lower nonwoven fabric sheet 22 of the topsheet 2 is substantially flat as illustrated in FIGS. 2 through 4. This flat configuration serves to avoid excessive bulkiness of the diaper 1 while maintaining the cushioning properties of the topsheet 2. As depicted in FIGS. 1 to 3, the lower nonwoven fabric sheet 22 has its longitudinal end edge 22e even with the longitudinal end edge e1 of the backsheet 3, one of the members forming the end flap 1E in the rear region 1A and the unshown front region. The end edge e1 is the end edge of the backsheet 3 irrespective of whether or not the end edge of the backsheet 3 and that of the side sheet 5 are even with each other.

As illustrated in FIG. 1, the projections 24 formed of the upper nonwoven fabric sheet 21 of the topsheet 2 longitudinally outwardly protrude beyond the end edge e1 of the backsheet 3 in the rear region 1A and the unshown front region. Therefore, the edge of the upper nonwoven fabric sheet 21 of the topsheet 2 is the most longitudinally distal of all the edges of other sheet materials constituting the end flap 1E. So configured, the end flap 1E of the diaper 1 of the embodiment is, even in contact with a wearer, less likely to feel strange or uncomfortable to wear because the projections 24 protruding beyond the end edge e1 serve as a cushion.

As illustrated in FIGS. 2 to 4, the projections 24 are created by the upper nonwoven fabric sheet 21 bulging away from the lower nonwoven fabric sheet 22 at the sites other than the bonds 23 so as to provide hollow spaces between the upper nonwoven fabric sheet 21 and the lower nonwoven fabric sheet 22. As illustrated in FIG. 2, the spaces inside the individual projections 24 arranged along the end edge e1 of the rear region 1A or the unshown front region are visible. That is, since the topsheet 2 has a hollow configuration due to the spaces inside the individual projections 24, it has high breathability and provides good cushioning to the skin.

As illustrated in FIG. 2, the topsheet 2 has a middle portion 2C and a pair of side portions 2S one on either side of the middle portion 2C. The middle portion 2C is located in a lateral middle portion of the diaper 1 and extends in the longitudinal direction X. Each side portion 2S adjoins the middle portion 2C and extends in the longitudinal direction X. The side portion 2S overlaps the side sheet 5 as illustrated in FIG. 1.

As illustrated in FIG. 1, the projections 24 include a plurality of first projections 41 located in the middle portion 2C and a plurality of second projections 42 located in the side portions 2S. The first and second projections 41 and 42 may have the same height or different heights. In the latter case, it is preferred that the first projections 41 be higher than the second projections 42, whereby it is easier to make the amount of protrusion of the first projections 41 greater than that of the second projections 42 in the longitudinal direction X. This will bring about further improves the cushioning properties of the front region where friction against the wearer's skin tends to increase with a change in wearer's abdominal circumference during wear. In the rear region 1A, too, the discomfort due to the contact of the end flap 1E with the wearer's skin will be further reduced. From the standpoint of reducing wearer discomfort, it is particularly preferred but not always necessary in the embodiment that the projections 24 protrude beyond the end edge e1 over the whole length of the end edge e1.

As illustrated in FIGS. 3 and 4, comparison between the first projections 41 and the second projections 42 shows that the individual first projections 41 have a larger area of space than the individual second projections 42. As used herein, the term "area of space" means the cross-sectional area of the space when the end edge e1 of the backsheet 3 in the rear region 1A and the front region is seen along the lateral direction. Such a configuration further improves the cushioning properties of the front region where friction against the wearer's skin tends to increase with a change in wearer's abdominal circumference during wear. In the rear region 1A, too, the wearer discomfort caused by the contact with the end flap 1E is further reduced.

With a view to enhancing the above discussed effect of the present invention, the ratio of the height L2 (FIG. 4) of the second projection 42 to the height L1 (FIG. 3) of the first projection 41, L2/L1, is preferably 0.2 or greater, more preferably 0.5 or greater, and preferably smaller than 1.0, more preferably 0.8 or smaller. The height L1 of the first projection 41 is preferably 0.7 mm or greater, more preferably 1.0 mm or greater, and preferably 3.0 mm or smaller, more preferably 2.0 mm or smaller. The height L2 of the second projection 42 is preferably 0.5 mm or greater, more preferably 0.7 mm or greater, and preferably 2.0 mm or smaller, more preferably 1.5 mm or smaller. The heights of the projections 41 and 42 can be measured by the method below.

Method for Measuring Height of Projections 41 and 42 of Topsheet:

A topsheet 2 to be measured is cut along the lateral direction with a sharp razor blade. The cut surface is observed with any means, such as the naked eye or an optical microscope, to measure the heights of the top of the projections 24 on the skin facing side of the topsheet 2 with no load applied thereto. When an optical microscope is used, the cut surface is observed at a magnification of 20 to 100 times using, e.g., VHX-100 from Keyence.

In order to improve the feel to the touch of the topsheet 2 during wear, the plan view area of the individual first projections 41 is preferably 5 mm$^2$ or larger, more preferably 10 mm$^2$ or larger, and preferably 30 mm$^2$ or smaller, more preferably 25 mm$^2$ or smaller, and that of the individual second projections 42 is preferably 1 mm$^2$ or larger, more preferably 3 mm$^2$ or larger, and preferably 20 mm$^2$ or smaller, more preferably 10 mm$^2$ or smaller.

For the same purpose, the first projections 41 protrude from the end edge e1 preferably by a length of 2 mm or more, more preferably 3 mm or more, and preferably 10 mm or less, more preferably 5 mm or less. The second projections 42 protrude from the end edge e1 preferably by a length of 1 mm or more, more preferably 2 mm or more, and preferably 5 mm or less, more preferably 3 mm or less. The lengths of the protruding portions (hereinafter "protrusions") of the projections 41 and 42 are measured as follows.

Method for Measuring Length of Protrusion of Projections 24:

The end portion each of the rear region 1A and the unshown front region of the absorbent article is cut along the longitudinal direction X of the absorbent article with a sharp razor blade. The cut surface is observed using an optical microscope to measure the length of the protrusion of the projection 24 from the end edge e1 with no load applied thereon. Observation may be conducted using, for example, VHX-100 from Keyence at a magnification of 20 to 100 times.

The topsheet 2 having the above described structure can be manufactured using, for example, the apparatus illustrated in FIG. 2 of JP 2005-111908A. The apparatus includes a first roller and a second roller that are arranged in mesh with each other. The apparatus further includes an anvil roller arranged in contact with the peripheral surface of the first roller. A continuous web of upper nonwoven fabric sheet 21 is introduced into the nip of the intermeshing first and second rollers to three-dimensionally deform the first nonwoven fabric sheet 21. Because the upper nonwoven fabric sheet 21 decreases in length as it is deformed three-dimensionally, the web of the first nonwoven fabric sheet 21 is preferably fed at a higher speed than a continuous web of lower nonwoven fabric sheet 22 so as to form highly cushioning projections 24. The deformed upper nonwoven fabric sheet 21 coming out of the nip is further transported as held to the peripheral surface of the first roller and joined with the lower nonwoven fabric sheet 22. The joined sheets are pressed under heat between the projections of the first roller and a heat roller which is the anvil roller, whereby the upper nonwoven fabric sheet 21 and the lower nonwoven fabric sheet 22 are bonded together in parts to produce the topsheet 2. Since the web of upper nonwoven fabric sheet 21 is fed at a higher rate than the web of lower nonwoven fabric sheet 22, the length of the upper nonwoven fabric sheet 21 in the transport direction is longer than that of the lower nonwoven fabric sheet 22 before being joined together. A topsheet having the first projections 41 and the second projections 42 as the projections 24 is produced by making the three-dimensional pattern of the intermeshing first and second rollers and the bonding pattern of the first roller and the heat roller different between the axial middle portion and opposite side portions of these rollers.

The above described diaper 1 can be manufactured using an apparatus for producing an open-type disposable diaper in what we call a longitudinal feed system. Specifically, a continuous web of backsheet 3 is transported in one direction, and absorbent members 4 are disposed in succession on the moving backsheet 3 at intervals. A continuous web of topsheet 2 is fed in the same transport direction as the backsheet 3 and superposed on the backsheet 3 having the absorbent member 4. The continuous web of topsheet 2 is three-dimensionally shaped on one side thereof and placed on the absorbent member 4 with the three-dimensional shaped side facing opposite to the absorbent member 4. The superposed topsheet 2, the absorbent member 4, and the backsheet 3 are bonded to one another to make a continuous web of individual diapers 1. In manufacturing diapers 1 having a pair of cuffs, it is preferable that a pair of side sheets 5 and 5 be fixed on opposed lateral sides of the topsheet 2 before the web of topsheet 2 is joined to the backsheet web. The continuous web of diapers 1 is severed between longitudinally adjacent absorbent members 4 across the width into discrete diapers 1 having predetermined dimensions using a known cutting means. When the continuous web of diapers 1 is severed, the transport tension is preferably made higher than usual. The severing position is preferably at and along the bonds between the upper nonwoven fabric sheet 21 and the lower nonwoven fabric sheet 22 of the topsheet 2. As a result of the severing step under these conditions, the projections of the topsheet 2 easily protrude outward beyond the end edge e1 of the end flap 1E. Since the length of the upper nonwoven fabric sheet 21 in the transport direction is longer than that of the lower nonwoven fabric sheet 22 in conformity with the three-dimensional deformation as stated earlier, the projections 24 formed of the upper nonwoven fabric sheet 21 are less likely to be collapsed even with a higher transport tension than usual applied to the continuous web of diapers 1 to be severed. Therefore, a sufficient amount of protrusion of the projections 24 is obtained.

The first nonwoven fabric sheet 21 and the second fabric sheet 22 may be formed of through-air, spun-bonded, hydroentangled, melt-blown, resin-bonded, and needle-punched nonwovens, and the like. A laminate of two or more of these nonwovens or a laminate of the nonwoven fabric and a resin film, and the like may be used. Preferred of them is through-air or spun-bonded nonwoven fabric. The basis weight of the nonwoven fabric is preferably 10 $g/m^2$ or more, more preferably 15 $g/m^2$ or more, and preferably 40 $g/m^2$ or less, more preferably 35 $g/m^2$. The first and second nonwoven fabric sheets 21 and 22 may be of the same or different nonwoven fabrics.

The backsheet 3 and the side sheet 5 may be formed of a sparingly liquid permeable film or spun-bonded/melt-blown/spun-bonded complex nonwoven fabric. The absorbent member 4 includes an absorbent core. The absorbent core may be made of airlaid hydrophilic fibers, such as cellulose fibers exemplified by pulp fiber, an airlaid mixture of hydrophilic fibers and an absorbent polymer, a layer of an absorbent polymer, or a stacked sheet structure composed of two absorbent sheets having an absorbent polymer sandwiched therebetween. The absorbent core may be covered on its skin facing side with a liquid permeable core wrap sheet or wrapped on its entire surface including the skin and non-skin facing sides with a core wrap sheet. The core wrap sheet may be a tissue layer made of hydrophilic fibers or liquid permeable nonwoven fabric.

Figure 5:
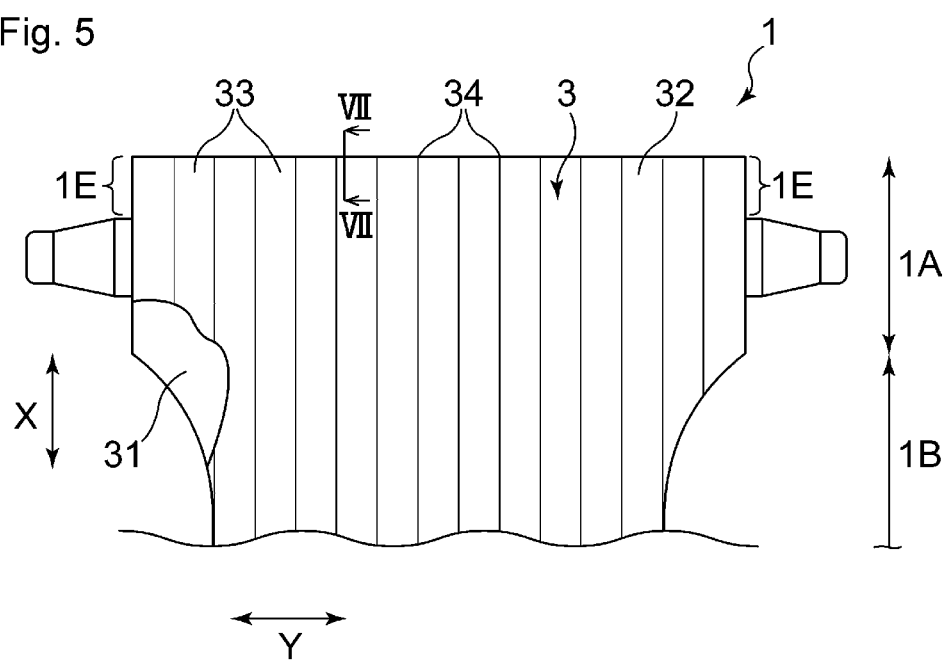
FIG. 5 is a schematic plan of an open-style disposable diaper as another embodiment of the present invention, seen from the non-skin facing side with part cut away.

The present invention will further be described on the basis of other preferred embodiments with reference to the accompanying drawings. FIG. 5 illustrates a schematic configuration of an open-type disposable diaper as another preferred embodiment of the present invention. The backsheet 3 of the illustrated diaper 1 has a laminate structure composed of a sparingly liquid permeable first sheet 31 and a second sheet 32 disposed on the non-skin facing side of the first sheet 31.

Figure 6:
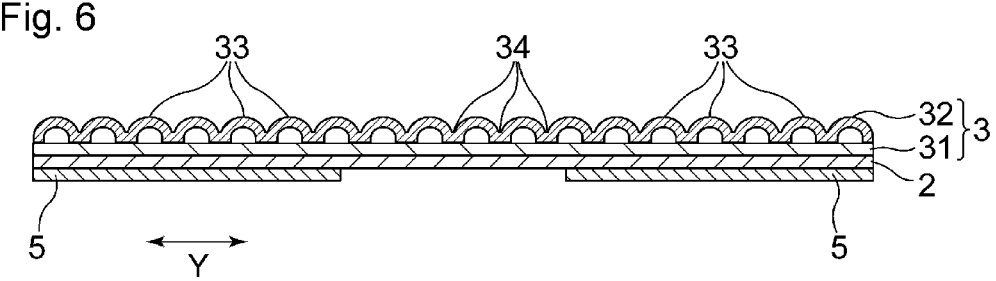
FIG. 6 is an end view of the end flap shown in FIG. 5.
Figure 7:
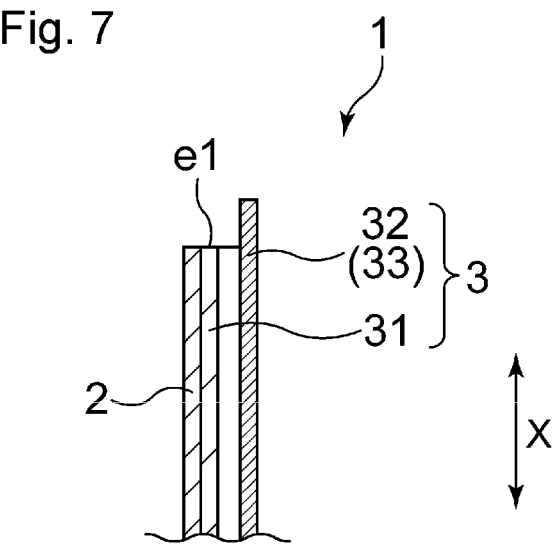
FIG. 7 is a cross-section taken along line VII-VII in FIG. 5.

As illustrated in FIGS. 5 through 7, the first sheet 31 is substantially flat. The first sheet 31 may be formed of a sparingly liquid permeable film. The second sheet 32 may be formed of nonwoven fabric, such as through-air or spun-bonded nonwoven fabric.

As illustrated in FIGS. 5 and 6, the second sheet 32 has a three-dimensional structure having second projections 33 and second recesses 34. In the embodiment shown in FIGS. 5 and 6 the second projections 33 project outward away from the first sheet 31 in a pattern forming ridges extending in the longitudinal direction X. The inside of the individual second projections 33 that is defined by the first sheet 31 and the second sheet 32 is hollow. The second recesses 34 are each a furrow formed between laterally adjacent ridge-shaped second projections 33 and 33 and extend in the longitudinal direction X. In short, the second sheet 32 has a corrugated shape. The second sheet 32 is bonded to the first sheet 31 via an adhesive (unshown) at the bottom of every second recess 34.

The diaper 1 of FIGS. 5 to 7 has an end flap 1E which is a longitudinal end portion of each of the rear region 1A and the unshown front region. The end flap 1E is composed of a topsheet 2, the backsheet 3, and a pair of side sheets 5. The longitudinal end edge el of the first sheet 31 of the backsheet 3 is even with the end edges of the side sheets 5 and the topsheet 2. In this embodiment, the end edge el is the end edge of the first sheet 31 irrespective of whether or not the end edges of the first sheet 31, the topsheet 2, and the side sheets 5 are even with each other.

In the embodiment shown in FIGS. 5 to 7, the second projections 33 formed of the second sheet 32 of the backsheet 3 longitudinally outwardly protrude beyond the end edge el of the first sheet 31 in the rear region 1A and the unshown front region as depicted in FIG. 7. Therefore, the edge of the second sheet 32 is the most longitudinally distal of all the edges of the other sheet materials constituting the end flap 1E. So configured, the end flap E of the diaper 1 of the embodiment is, even in contact with a wearer, less likely to cause wearer discomfort while worn because the second projections 33 protruding beyond the end edge el serve as a cushion.

With a view to enhancing the above discussed effect of the present invention, the height of the second projection 33 is preferably 0.2 mm or greater, more preferably 0.4 mm or greater, and preferably 3 mm or smaller, more preferably 2 mm or smaller. The height of the second projection 33 can be measured in the same manner as for the projections 41 and 42. With the same view as above, the second projection 33 protrudes beyond the end edge el preferably by a length of 1 mm or more, more preferably 3 mm or more, and preferably 10 mm or less, more preferably 5 mm or less. The length of the protruded portion (hereinafter "protrusion") of the second projection 33 can be measured in the same manner as for the measurement of the length of the protrusion of the projections 41 and 42.

The corrugated second sheet 32 is formed by, for example, applying an adhesive in stripes to one side of one of two sheets, designated sheet A, under tension, joining the other sheet, designated sheet B, under higher tension compared with the sheet A to the adhesive-coated side of the sheet A, and making the tension applied to the resulting laminate lower than that applied to the sheet B.

The above method will be elaborated more specifically taking, for instance, the first sheet 31 and the second sheet 32 that constitute the diaper 1. An adhesive is applied to one side of a continuous web of second sheet 32 in stripes extending in the web transport direction, preferably extending a direction along the web transport direction. There are thus provided adhesive coated regions and adhesive uncoated regions alternating in a direction intersecting the web transport direction, preferably a direction perpendicular to the web transport direction.

Subsequently, the second sheet 32 moving with a tension applied in the transport direction is joined to a web of first sheet 31 moving in the same direction as the second sheet 32 to make a laminate sheet. The transport tension applied to the second sheet 32 is higher than that applied to the first sheet 31. The resulting laminate sheet is sent to a downstream step under a transport tension lowered to the tension having been applied to the moving first sheet 31.

After the two sheets are joined together into a laminate sheet, since the transport tension applied to the second sheet 32 is lower than before, the second sheet 32 is relieved from the highly tensioned state. As a result, the second sheet 32 increases in width in the transverse direction Y and, at the same time, bulges away from the first sheet 31 in the adhesive uncoated regions to form ridge-shaped second projections 33 extending in the direction of adhesive application. The adhesive coated regions of the second sheet 32 remain fixed to the first sheet 31 to become furrow-like second recesses 34. There is thus formed the corrugated second sheet 32.

In the case where the second sheet 32 is composed of a plurality of sheet materials, an adhesive is applied to the skin facing side of an inner sheet of the second sheet 32 in stripes, and the adhesive coated side of the inner sheet is joined with another sheet that is transported under a high tension. Thereafter, the other sheet is relieved from the transport tension to form ridges and furrows. It is preferred that at least the other sheet be through-air nonwoven fabric.

Similarly to the diaper 1 shown in FIG. 1, the diaper 1 of FIGS. 5 through 7 can be manufactured using an apparatus for producing an open-type disposable diaper in a longitudinal feed system. Specifically, a continuous web of backsheet 3 is provided. The backsheet 3 has ridge-shaped second projections 33 and furrow-shaped second recesses 34 extending in the transport direction. Absorbent members 4 are disposed in succession on the first sheet 31 of the moving backsheet 3 at intervals in the transport direction. Each absorbent member 4 is placed on the side of the first sheet 31 opposite to the second sheet 32. A continuous web of topsheet 2 is transported in the same direction as the backsheet 3 and superposed on the side of the backsheet 3 having the absorbent member 4. The topsheet 2 and the absorbent member 4, the absorbent member 4 and the backsheet 3, and the topsheet 2 and the backsheet 3 are bonded to each other thereby to make a continuous web of diapers 1. The continuous web of diapers 1 is severed between longitudinally adjacent absorbent members 4 across the width into discrete diapers 1 having predetermined dimensions using a known cutting means. When the continuous web of diapers 1 is severed, the transport tension is preferably made higher than usual. As a result of the severing step under this condition, the second projections 33 of the second sheet 32 are allowed to protrude outward easily beyond the end edge el of the end flap 1E.

Figure 8:
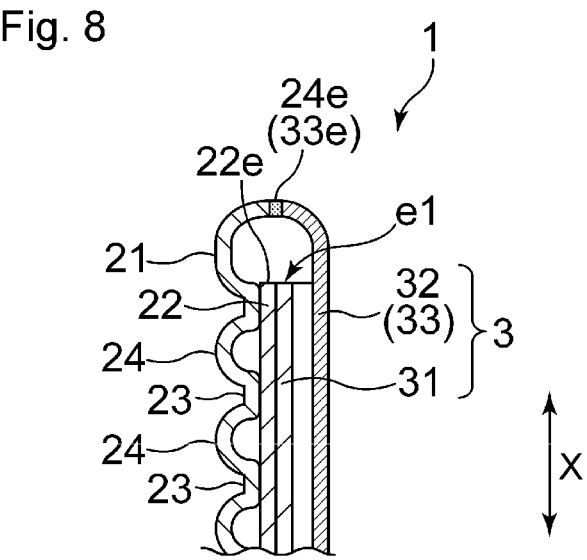
FIG. 8 is a schematic cross-section of an end flap of a disposable diaper according to still another embodiment of the present invention, taken along the longitudinal direction of the diaper.

FIG. 8 schematically illustrates an essential part of an open-type disposable diaper as still another preferred embodiment of the present invention. The backsheet 3 of the diaper 1 illustrated has a laminate structure composed of a first sheet 31 and a second sheet 32. The topsheet 2 of the diaper 1 also has a laminate structure composed of an upper nonwoven fabric sheet 21 having projections 24 and a lower nonwoven fabric sheet 22. The end flap 1E of this diaper 1 is composed of the topsheet 2, the backsheet 3, and side sheets 5. In this embodiment, the longitudinal end edge el of the first sheet 31 of the backsheet 3 is even with the end edge 22e of the lower nonwoven fabric sheet 22 of the topsheet 2 and the end edges of the side sheets 5.

In the embodiment of FIG. 8, the second projections 33 of the second sheet 32 of the backsheet 3 protrude longitudinally outward beyond the end edge el of the first sheet 31 in each of the rear region 1A and the unshown front region. In addition, the projections 24 of the upper nonwoven fabric sheet 21 of the topsheet 2 protrude longitudinally outward beyond the end edge el of the first sheet 31. So configured, the end flap 1E of the diaper 1 of the embodiment is, even in contact with the skin of a wearer, less likely to cause wearer discomfort while worn because the projections 24 and the second projections 33 protruding beyond the end edge el serve as a cushion. In order to improve the appearance of the diaper 1, it is preferred that the edges 24e of the protrusions of the projections 24 protruding from the end edge el and the edges 33e of the protrusions of the second projections 33 protruding from the end edge el be bonded to each other. From the standpoint of the feel to the touch, the bonding is preferably done not by fusion but by pressure bonding.

While the present invention has been described on the basis of its embodiments, it should be understood that the present invention is not limited thereto, and alterations can be made therein.

For example, while in the foregoing embodiments the three-dimensional structure of the topsheet 2 is created by using two sheets of nonwoven fabric, i.e., the upper nonwoven fabric sheet 21 and the lower nonwoven fabric sheet 22, the three-dimensional structure may be formed of a single sheet of nonwoven fabric.

While the three-dimensionally shaped topsheet 2 used in the foregoing embodiments has discretely arranged projections 24, the topsheet 2 may have a three-dimensional structure composed of ridges and furrows or grooves alternately extending in one direction on the skin facing side, such as disclosed in JP 8-302555A.

While the projections 24 of the topsheet 2 in the foregoing embodiments include first projections 41 and second projections 42, all the projections 24 may have the same height, or the projections 24 may have random heights. Projections 24 of the same height may all have the same cross-sectional area of the inside space or may have various space areas.

While in the foregoing embodiments the projections 24 longitudinally outward protrude beyond the end edge el of the backsheet 3 and the side sheets 5 in both of the rear region 1A and the unshown front region, it is only necessary for the projections 24 to protrude beyond the end edge el in at least one of the rear region 1A and the front region.

Examples of the absorbent article of the present invention include, but are not limited to, open-type disposable diapers as described, pull-on disposable diapers, sanitary napkins, and incontinence pads.

The following clauses are considered further descriptive of the absorbent articles disclosed herein.

1. An absorbent article including a three-dimensionally shaped topsheet having projections and recesses and a backsheet, having a longitudinal direction corresponding to the front-to-back direction of a wearer and a lateral direction perpendicular to the longitudinal direction, and having opposed longitudinal end portions, the longitudinal end portions being formed of at least the topsheet and the backsheet, and a plurality of the projections of the topsheet protruding longitudinally outward beyond the end edge of the backsheet in at least one of the longitudinal end portions.

<2> The absorbent article as set forth in clause <1>, wherein the topsheet has a laminate structure composed of an upper nonwoven fabric sheet on the side facing the skin of a wearer and a lower nonwoven fabric sheet on the side away from the skin of a wearer, the upper and lower nonwoven fabric sheets being united at bonds, the projections being formed of the upper nonwoven fabric sheet bulging away from the lower nonwoven fabric sheet at sites other than the bonds, the upper nonwoven fabric sheet being longer than the lower nonwoven fabric sheet in the longitudinal direction before being united with the lower nonwoven fabric sheet, and the upper nonwoven fabric sheet protruding longitudinally outward beyond the end edge of the backsheet.

<3> The absorbent article as set forth in clause <2>, wherein a longitudinal end edge of the lower nonwoven fabric sheet is even with the end edge of the backsheet in plan view.

<4> The absorbent article as set forth in clause <2> or <3>, wherein the lower nonwoven fabric sheet is substantially flat.

<5> The absorbent article as set forth in any one of clauses <2> to <4>, wherein the projections are formed of the upper nonwoven fabric sheet bulging away from the lower nonwoven fabric sheet at the sites other than the bonds to create hollow spaces between the upper and the lower nonwoven fabric sheets, the spaces inside the individual projections arranged along the end edge of the backsheet being visible.

<6> The absorbent article as set forth in clause <5>, wherein the topsheet has a lateral middle portion and a side portion on either side of the lateral middle portion, and the individual projections have a larger cross-sectional area of their space in the lateral middle portion than in the side portion when the end edge of the backsheet is seen along the lateral direction.

<7> The absorbent article as set forth in any one of clauses <1> to <6>, wherein the topsheet has a lateral middle portion and a side portion on either side of the lateral middle portion, and the projections protrude longitudinally outward to a greater amount in the lateral middle portion than in the side portion.

<8> The absorbent article as set forth in any one of clauses <1> to <7>, having a front region, a rear region, and a crotch region between the front region and the rear region, wherein the projections of the topsheet protrude longitudinally outward beyond the end edge of the backsheet in at least one of the front region and the rear region.

<9> The absorbent article as set forth in any one of clauses <1> to <8>, having a front region, a rear region, and a crotch region between the front region and the rear region, wherein the projections of the topsheet protrude longitudinally outward beyond the end edge of the backsheet in both the front region and the rear region.

<10> An absorbent article including an absorbent member and a sparingly liquid permeable backsheet, having a longitudinal direction corresponding to the front-to-back direction of a wearer and a lateral direction perpendicular to the longitudinal direction, and having opposed longitudinal end portions, the longitudinal end portions being formed of at least the backsheet, the backsheet having a laminate structure including a sparingly liquid permeable first sheet and a second sheet on the non-skin facing side of the first sheet, the second sheet having a three-dimensional structure having second projections and second recesses, and a plurality of the second projections of the second sheet protruding longitudinally outward beyond the end edge of the first sheet in at least one of the longitudinal end portions.

<11> The absorbent article as set forth in clause <10>, further including a three-dimensionally shaped topsheet having projections and recesses, wherein the longitudinal end portions are formed of at least the topsheet and the backsheet, and a plurality of the projections of the topsheet protrude longitudinally outward beyond the end edge of the first sheet in at least one of the longitudinal end portions.

<12> The absorbent article as set forth in clause <10> or <11>, wherein the edges of the protrusions of the projections protruding from the end edge of the first sheet and the edges of the protrusions of the second projections protruding from the end edge of the first sheet are bonded to each other.

INDUSTRIAL APPLICABILITY

The absorbent article according to the present invention is less likely to cause wearer discomfort when its longitudinal end edge contacts the skin of a wearer.

The invention claimed is:

1. An absorbent article comprising a three-dimensionally shaped topsheet having projections and recesses and a backsheet, having a longitudinal direction corresponding to the front-to-back direction of a wearer and a lateral direction perpendicular to the longitudinal direction, and having opposed longitudinal end portions, the longitudinal end portions being formed of at least the topsheet and the backsheet, a plurality of the projections protruding longitudinally outward beyond an end edge of the backsheet in at least one of the longitudinal end portions, and the topsheet having a lateral middle portion and a side portion on either side of the lateral middle portion, and the projections protruding longitudinally outward to a greater amount in the lateral middle portion than in the side portion.

2. The absorbent article according to claim 1, wherein the topsheet has a laminate structure comprising an upper nonwoven fabric sheet on the side facing the skin of a wearer and a lower nonwoven fabric sheet on the side away from the skin of a wearer, the upper and lower nonwoven fabric sheets being united at bonds, the projections being formed of the upper nonwoven fabric sheet bulging away from the lower nonwoven fabric sheet at sites other than the bonds, the upper nonwoven fabric sheet being longer than the lower nonwoven fabric sheet in the longitudinal direction before being united with the lower nonwoven fabric sheet, and the upper nonwoven fabric sheet protruding longitudinally outward beyond the end edge of the backsheet.

3. The absorbent article according to claim 2, wherein the projections are formed of the upper nonwoven fabric sheet bulging away from the lower nonwoven fabric sheet at sites other than the bonds to create hollow spaces between the upper and the lower nonwoven fabric sheets, the spaces inside the individual projections arranged along the end edge of the backsheet being visible.

4. The absorbent article according to claim 3, wherein the topsheet has a lateral middle portion and a side portion on either side of the lateral middle portion, and the individual projections have a larger cross-sectional area of their space in the lateral middle portion than in the side portion when the end edge of the backsheet is seen along the lateral direction.

5. An absorbent article comprising a three-dimensionally shaped topsheet having projections and recesses and a backsheet, having a longitudinal direction corresponding to the front-to-back direction of a wearer and a lateral direction perpendicular to the longitudinal direction, and having opposed longitudinal end portions, the topsheet having a laminate structure comprising an upper nonwoven fabric sheet on the side facing the skin of a wearer and a lower nonwoven fabric sheet on the side away from the skin of a wearer, the upper and lower nonwoven fabric sheets being united at bonds, the projections being formed of the upper nonwoven fabric sheet bulging away from the lower nonwoven fabric sheet at sites other than the bonds, the projections being formed of the upper nonwoven fabric sheet bulging away from the lower nonwoven fabric sheet at sites other than the bonds to create hollow spaces between the upper and the lower nonwoven fabric sheets, the spaces inside the individual projections arranged along the end edge of the backsheet being visible, the topsheet having a lateral middle portion and a side portion on either side of the lateral middle portion, and the individual projections having a larger cross-sectional area of their space in the lateral middle portion than in the side portion when the end edge of the backsheet is seen along the lateral direction, the upper nonwoven fabric sheet being longer than the lower nonwoven fabric sheet in the longitudinal direction before being united with the lower nonwoven fabric sheet, and the upper nonwoven fabric sheet protruding longitudinally outward beyond the end edge of the backsheet, the longitudinal end portions being formed of at least the topsheet and the backsheet, and a plurality of the projections protruding longitudinally outward beyond an end edge of the backsheet in at least one of the longitudinal end portions.

6. The absorbent article according to claim 2, wherein a longitudinal end edge of the lower nonwoven fabric sheet is even with an end edge of the backsheet in plan view.

7. The absorbent article according to claim 2, wherein the lower nonwoven fabric sheet is substantially flat.

8. The absorbent article according to claim 1, having a front region, a rear region, and a crotch region between the front region and the rear region, wherein the projections of the topsheet protrude longitudinally outward beyond the end edge of the backsheet in at least one of the front region and the rear region.

9. The absorbent article according to claim 1, having a front region, a rear region, and a crotch region between the front region and the rear region, wherein the projections of the topsheet protrude longitudinally outward beyond the end edge of the backsheet in both the front region and the rear region.

* * * * *